United States Patent
Kim et al.

(10) Patent No.: US 10,806,684 B2
(45) Date of Patent: Oct. 20, 2020

(54) COSMETIC COMPOSITION CONTAINING ORGANIC-INORGANIC COMPOSITE PARTICLES FOR BLOCKING NEAR INFRARED RAYS

(71) Applicants: COSMAX INC., Hwaseong-si, Gyeonggi-do (KR); IUCF-HYU (INDUSTRY-UNIVERSITY COOPERATION FOUNDATION HANYANG UNIVERSITY), Seongdong-gu, Seoul (KR)

(72) Inventors: Su Ji Kim, Seongnam-si (KR); Jun Bae Lee, Seongnam-si (KR); Chun Ho Park, Seongnam-si (KR); Youn Joon Kim, Seongnam-si (KR); Kweon Jong Yoo, Suwon-si (KR); Myeong Sam Park, Seoul (KR); Eun Chul Cho, Seoul (KR); Seong Uk Kim, Daejeon (KR); Min Gyu Kim, Seoul (KR); Nu Ri Han, Seoul (KR)

(73) Assignees: COSMAX INC., Gyeonggi-do (KR); IUCF-HYU (INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 203 days.

(21) Appl. No.: 16/073,968

(22) PCT Filed: Nov. 30, 2017

(86) PCT No.: PCT/KR2017/013915
§ 371 (c)(1),
(2) Date: Jul. 30, 2018

(87) PCT Pub. No.: WO2019/066142
PCT Pub. Date: Apr. 4, 2019

(65) Prior Publication Data
US 2020/0146952 A1    May 14, 2020

(30) Foreign Application Priority Data

Sep. 29, 2017    (KR) .................. 10-2017-0128315

(51) Int. Cl.
*A61K 8/29*      (2006.01)
*A61K 8/19*      (2006.01)
(Continued)

(52) U.S. Cl.
CPC .................. *A61K 8/29* (2013.01); *A61K 8/19* (2013.01); *A61K 8/26* (2013.01); *A61K 8/27* (2013.01);
(Continued)

(58) Field of Classification Search
None
See application file for complete search history.

(56) References Cited

U.S. PATENT DOCUMENTS

| 7,247,378 B2 | 7/2007 | Kim et al. |
| 2003/0091824 A1* | 5/2003 | Kim .................. C08L 51/10 428/404 |
| 2018/0042823 A1 | 2/2018 | Lee et al. |

FOREIGN PATENT DOCUMENTS

| JP | 2006-137704 A | 6/2006 |
| JP | 2007-238353 A | 9/2007 |

(Continued)

OTHER PUBLICATIONS

JP2006137704 Machine Translation from Innovation Q, 2006 document, translation made Apr. 15, 2020, 7 pages. (Year: 2006).*

(Continued)

Primary Examiner — Trevor Love
(74) Attorney, Agent, or Firm — Buchanan Ingersoll & Rooney PC

(57) ABSTRACT

Provided is a cosmetic composition including organic-inorganic composite particles for blocking near-infrared rays.
(Continued)

When the cosmetic composition for blocking near-infrared rays according to the present disclosure is applied to skin, light in the near-infrared region may be significantly blocked. The cosmetic composition may be used as a multifunctional product in combination with a UV-blocking material to block a wide range of wavelengths adversely affecting the skin, thereby preventing skin aging.

9 Claims, 2 Drawing Sheets

(51) Int. Cl.
*A61K 8/26* (2006.01)
*A61K 8/27* (2006.01)
*A61K 8/28* (2006.01)
*A61K 8/81* (2006.01)
*A61Q 17/04* (2006.01)
*A61K 8/02* (2006.01)
*A61Q 19/08* (2006.01)
*A61K 8/06* (2006.01)

(52) U.S. Cl.
CPC .............. *A61K 8/28* (2013.01); *A61K 8/8147* (2013.01); *A61Q 17/04* (2013.01)

(56) References Cited

FOREIGN PATENT DOCUMENTS

| KR | 10-1999-0028949 A | 4/1999 |
| KR | 10-2003-0020515 A | 3/2003 |
| KR | 10-2014-0030395 A | 3/2014 |
| KR | 10-1648676 B1 | 8/2016 |
| KR | 10-2016-0124726 A | 10/2016 |
| WO | 97/02806 A1 | 1/1997 |

OTHER PUBLICATIONS

Korean International Search Report dated Jun. 12, 2018, by the Korean Patent Office in corresponding Korean International Application No. PCT/KR2007/013915. (3 pages).

* cited by examiner

COSMETIC COMPOSITION CONTAINING ORGANIC-INORGANIC COMPOSITE PARTICLES FOR BLOCKING NEAR INFRARED RAYS

TECHNICAL FIELD

The present disclosure relates to a cosmetic composition including organic-inorganic composite particles for blocking near-infrared rays.

BACKGROUND ART

Skin aging is divided into two processes: intrinsic aging, which is a natural aging process, and extrinsic aging which is caused by various environmental factors. Extrinsic aging may be also called photoaging because its main cause is light. Unlike intrinsic aging that occurs as a result of aging, extrinsic aging refers to phenomena such as deep wrinkles, rough skin, reduced skin elasticity, etc. which are caused by continuous long periods of exposure to sunlight.

Sunlight reaching the earth's surface is largely divided into ultraviolet rays (UVB and UVA), visible rays, and infrared rays (IR-A, IR-B, and IR-C). Among infrared rays, most of the infrared rays reaching the ground are near-infrared rays (IR-A). As is well known, ultraviolet rays penetrate the epidermis and dermis to cause a variety of skin aging such as erythema, skin cancer, etc. However, near-infrared rays penetrate into the subcutaneous adipose layer much deeper than UVA, reaching the deep dermis, thereby causing collagen tissue destruction, reactive oxygen production, and vasodilation, leading to fundamental skin aging such as loss of elasticity, etc. Until now, many studies has been conducted on ultraviolet rays as a main cause of photoaging, and accordingly, numerous studies have been conducted on organic/inorganic blocking agents to protect the skin from ultraviolet rays. Products developed using these UV-blocking organic/inorganic materials, of which UV blocking ability is expressed by indices such as SPF and PA, are being applied to various products. However, since not only ultraviolet rays but also infrared rays have recently been recognized as one of the main causes of skin aging, there have been many reports regarding studies on infrared rays and skin. Accordingly, there is an increasing interest in the development of infrared ray-blocking products.

According to current research trends, skin aging phenomena caused by near-infrared rays have been studied, but there is little research on the development of materials and products for blocking near-infrared rays.

DESCRIPTION OF EMBODIMENTS

Technical Problem

An aspect provides a cosmetic composition for blocking near-infrared rays, the cosmetic composition including organic-inorganic composite particles for blocking near-infrared rays, wherein the organic-inorganic composite particles include a polymer matrix and inorganic nanoparticles dispersed in the polymer matrix, and have a hollow spherical form having a predetermined thickness.

Another aspect provides a method of preparing the cosmetic composition for blocking near-infrared rays, the method including mixing an oil phase with the organic-inorganic composite particles for blocking near-infrared rays, wherein the organic-inorganic composite particles for blocking near-infrared rays include the polymer matrix and the inorganic nanoparticles dispersed in the polymer matrix, and have a hollow spherical form having a predetermined thickness; dissolving the mixture by heating at 50° C. to 100° C., and adding an aqueous phase to the solution dissolved by heating, followed by stirring.

Solution to Problem

An aspect provides a cosmetic composition for blocking near-infrared rays, the cosmetic composition including organic-inorganic composite particles for blocking near-infrared rays, wherein the organic-inorganic composite particles include a polymer matrix; and inorganic nanoparticles dispersed in the polymer matrix, and have a hollow spherical form having a predetermined thickness.

The organic-inorganic composite particles for blocking near-infrared rays, which are an active ingredient of the cosmetic composition for blocking near-infrared rays according to the present disclosure, are characterized in that they have a hollow structure having an empty space inside thereof and are formed in a spherical shape, as observed under an optical microscope and a scanning electron microscope. Since the organic-inorganic composite particles have the hollow structure having an empty space inside thereof, a light scattering effect may be improved due to a difference in a refractive index between the empty space inside thereof and the shell of the organic-inorganic composite particles, thereby improving the effect of blocking near-infrared rays. Therefore, according to one embodiment of the present disclosure, a ratio of a radius to the thickness of each of the organic-inorganic composite particles is 2:1 to 4:1, wherein the radius is a radius from the center to the outermost point of each of the organic-inorganic composite particles.

Preferably, the outer circumferential surface and the inner circumferential surface of the organic-inorganic composite particles for blocking near-infrared rays may have high roughness, and the high roughness of the surface improves diffraction and reflection properties of light, and as a result, light scattering characteristics of the infrared region may be increased to bring about an effect of improving near-infrared ray-blocking performance. Therefore, according to another embodiment of the present disclosure, a root mean square (RMS) surface roughness of an outer circumferential surface of each of the organic-inorganic composite particles may be 10 nm to 50 nm. Further, according to still another embodiment of the present disclosure, the RMS surface roughness of an inner circumferential surface of each of the organic-inorganic composite particles may be 5 nm to 30 nm.

The surface roughness of the organic-inorganic composite particles varies depending on the content of the inorganic nanoparticles, and therefore, the content of the inorganic nanoparticles is preferably 1% by weight to 5% by weight, based on the total weight of the organic-inorganic composite particles. In this regard, when the content of the inorganic nanoparticles is less than the lower limit, or more than the upper limit, there is a problem in that the surface roughness value of the organic-inorganic composite particles is lowered to reduce light scattering characteristics of the particles, leading to a decrease in the near-infrared ray-blocking effect. Further, when the content of the inorganic nanoparticles is more than the upper limit, there is a problem in that aggregates of the inorganic nanoparticles are formed in the organic-inorganic composite particles to decrease the near-infrared ray-blocking effect of the composite particles. Accordingly, according to still another embodiment of the present disclosure, the content of the inorganic nanoparticles may be preferably 1% by weight to 5% by weight, based on the total weight of the organic-inorganic composite particles.

The term "inorganic nanoparticles" are not particularly limited, as long as they are nanoparticles that are dispersed in the polymer matrix to constituting the organic-inorganic composite particles. For example, the inorganic nanoparticles may be selected from the group consisting of $TiO_2$, $ZnO$, $ZnO_2$, $CuO$, $CuO_2$, $Al_2O_3$, $Al(OH)_3$, $CeO_2$, $Ce_2O_3$, $Fe_2O_3$, $ZrO_2$, and any mixture thereof. Further, when the inorganic nanoparticles are non-spherical nanoparticles having a size of 100 nm to 500 nm, the near-infrared ray-blocking ability may be further improved.

According to still another embodiment of the present disclosure, the polymer matrix is not particularly limited, as long as it is a polymer matrix capable of dispersing inorganic nanoparticles, and for example, the polymer matrix may be selected from the group consisting of polystyrene, poly (methyl methacrylate), polymethylacrylate, polyethylacrylate, polypropylacrylate, polyisopropylacrylate, polyethylmethacrylate, polybutylacrylate, polybutylmethacrylate, polypentylacrylate, polypentylmethacrylate, polyglycidylmethacrylate, polycyclohexylacrylate, poly(2-ethylhexylacrylate), polyacrylic acid, polymethacrylic acid, and any mixture thereof.

According to one embodiment of the present disclosure, the polymer matrix may be poly(methyl methacrylate) (PMMA), and the inorganic nanoparticles may be $TiO_2$. In a specific embodiment, when the near-infrared ray-blocking ability of the organic-inorganic composite particles including $TiO_2$ inorganic nanoparticles dispersed in an MMA monomer solution containing 20 wt % PMMA is examined, excellent light-blocking ability is observed in the infrared region of 400 nm to 1250 nm, and in particular, excellent light-blocking ability is also observed in the near-infrared region of 900 nm to 1250 nm.

Further, plasmonic nanoparticles or plasmonic nanofilm may be attached to the surface of each of the inorganic nanoparticles. In this regard, since light absorption and scattering wavelength due to localized surface plasmon resonance of plasmon nanoparticles may be controlled according to a size and spacing of the plasmonic nanoparticles or the plasmonic nanofilm attached to the surface, the near-infrared ray-blocking ability of the organic-inorganic composite particles according to the present disclosure may be controlled. Therefore, according to still another embodiment of the present disclosure, the plasmonic nanoparticles or plasmonic nanofilm may be attached to the surface of the inorganic nanoparticles.

In this regard, the plasmonic nanoparticles and the plasmonic nanofilm may be selected from gold, silver, platinum, palladium, copper, and aluminum. The size of the plasmonic nanoparticles may be controlled by amounts of a metal salt and a reducing agent which are added during a preparation process thereof, and a shape of the plasmonic nanoparticles is not particularly limited, but may be preferably selected from spherical, bar, wire, pyramidal, cubic, and prismatic forms.

The organic-inorganic composite particles for blocking near-infrared rays may be prepared by (a) dispersing inorganic nanoparticles in a mixed solution of a monomer compound and a crosslinking agent; (b) adding an initiator to the inorganic nanoparticle-dispersed solution; and (c) adding the initiator-added dispersion to a stabilizer aqueous solution at 60° C. to 90° C. to emulsifying the solution, but is not limited thereto. According to one embodiment of the present disclosure, a linear polymer substance may be further added to the mixed solution of (a). In this regard, a content of the linear polymer substance to be added may be 15% by weight to 25% by weight, based on the weight of the monomer compound.

Further, the linear polymer substance may be selected from the group consisting of polystyrene, poly(methyl methacrylate), polymethylacrylate, polyethylacrylate, polypropylacrylate, polyisopropylacrylate, polyethylmethacrylate, polybutylacrylate, polybutylmethacrylate, polypentylacrylate, polypentylmethacrylate, polyglycidylmethacrylate, polycyclohexylacrylate, poly(2-ethylhexylacrylate), polyacrylic acid, polymethacrylic acid, and mixtures thereof.

According to still another embodiment of the present disclosure, the monomer compound may be selected from styrene, methyl methacrylate, methylacrylate, ethylacrylate, propylacrylate, isopropylacrylate, ethylmethacrylate, butylacrylate, butylmethacrylate, pentylacrylate, pentylmethacrylate, glycidylmethacrylate, cyclohexylacrylate, 2-ethylhexylacrylate, acrylic acid, methacrylic acid, and mixtures thereof.

According to still another embodiment of the present disclosure, the crosslinking agent may be selected from ethyleneglycoldimethacrylate, 1,2-ethanedioldiacrylate, 1,3-propanedioldiacrylate, 1,3-butanedioldiacrylate, 1,4-butanedioldiacrylate, 1,5-pentanedioldiacrylate, 1,6-hexanedioldiacrylate, ethyleneglycoldiacrylate, propyleneglycoldiacrylate, butyleneglycoldiacrylate, triethyleneglycoldiacrylate, polyethyleneglycoldiacrylate, polypropyleneglycoldiacrylate, polybutyleneglycoldiacrylate, alkylacrylate, 1,2-ethanedioldimethacrylate, 1,3-propanediolmethacrylate, 1,3-butanedioldimethacrylate, propyleneglycoldimethacrylate, butyleneglycoldimethacrylate, triethyleneglycoldimethacrylate, polyethyleneglycoldimethacrylate, polypropyleneglycoldimethacrylate, polybutyleneglycoldimethacrylate, allylmethacrylate, urethane acrylate, diallyl malate, and mixtures thereof.

According to still another embodiment of the present disclosure, the initiator may be selected from 2,2-azobisisobutyronitrile (AIBN), 2,2-azobis(2-methylisobutyronitrile), 2,2-azobis(2,4-dimethylvaleronitrile), benzoylperoxide, laurylperoxide, cumene hydroperoxide, methyl ethyl ketone peroxide, t-butyl hydroperoxide, o-chlorobenzoyl peroxide, o-methoxybenzoyl peroxide, t-butylperoxy-2-ethylhexanoate, t-butylperoxyisobutyrate, and mixtures thereof.

According to still another embodiment of the present disclosure, the stabilizer aqueous solution may be selected from a polyvinylalcohol (PVA) aqueous solution, a dioctylsodiumsulfosuccinate aqueous solution, a sodiumdodecylsulfate aqueous solution, a cetyl trimethylammoniumbromide aqueous solution, and mixtures thereof.

The cosmetic composition for blocking near-infrared rays according to the present disclosure may be prepared in any formulation commonly prepared in the art. Product forms may include makeup cosmetics such as lipsticks, lip gloss, lip balm, eye shadow, etc.; hair cosmetics such as hair sticks, pomades, etc.; basic cosmetics such as moisturizing gels, moisturizing creams, emulsions, serum, lotions, creams, liquid foundations, solid foundation formulations, etc.

Further, the cosmetic composition for blocking near-infrared rays according to the present disclosure may be any one formulation of an oil-in-water type, a water-in-oil type, and a non-aqueous dispersion. The term "oil-in-water (O/W)" may be used interchangeably with "oil-in-water emulsion", and refers to a form in which oil is dispersed in water. The term "water-in-oil (W/O)" may be used interchangeably with "water-in-oil emulsion", and refers to a form in which water is dispersed in oil. The term "non-aqueous dispersion" refers to those dispersed in a solvent other than water. In a specific embodiment, the cosmetic composition for blocking near-infrared rays according to the present disclosure may be prepared in the water-in-oil type in order to optimize the near-infrared ray-blocking functionality of the organic-inorganic composite particles.

The cosmetic composition according to a specific embodiment may further include additional components commonly used in cosmetics, for example, any common cosmetic component selected from purified water, a moisturizer, an emulsifier, a thickening agent, a dispersing agent, a color, a fragrance, a filler, a preservative, a neutralizing agent, a UV-blocking agent, a sweetener, vitamins, an antioxidant, a free-radical scavenger, a sequestering agent, and mixtures thereof. In a specific embodiment, the cosmetic composition for blocking near-infrared rays according to the present disclosure may further include a UV blocking agent to maximize the effect of preventing skin aging, but is not limited thereto.

A person skilled in the art will take care to select any additional components and/or their amounts such that the beneficial properties of the composition according to the present disclosure are not, or are not substantially, adversely affected by the envisaged addition. A blending amount of the additional component may be easily selected by a person skilled in the art within the scope that does not impair the objects and effects of the present disclosure, and the blending amount may be about 0.001% by weight to about 30% by weight, specifically about 0.01% by weight to about 10% by weight, based on the total weight of the composition. According to one embodiment of the present disclosure, the present disclosure may be a cosmetic composition for blocking near-infrared rays including distilled water, a base for cosmetics, and the organic-inorganic composite particles for blocking near-infrared rays as an active ingredient.

Another aspect provides a method of preparing the cosmetic composition for blocking near-infrared rays, the method including mixing an oil phase with the organic-inorganic composite particles for blocking near-infrared rays, wherein the organic-inorganic composite particles for blocking near-infrared rays include the polymer matrix and the inorganic nanoparticles dispersed in the polymer matrix, and have a hollow spherical form having a predetermined thickness; dissolving the mixture by heating at 50° C. to 100° C., and adding an aqueous phase to the solution dissolved by heating, followed by stirring.

The term "oil phase" means an oily solvent and a portion dissolved in the oily solvent, and it is possible to use any oil phase which is an oily solvent disclosed in the public and which may be easily substituted by a person skilled in the art.

The term "aqueous phase" means an aqueous solvent and a portion dissolved in the aqueous solvent, and in a specific embodiment, the aqueous phase may be purified water, but is not limited thereto.

The mixing of the oil phase with the organic-inorganic composite particles for blocking near-infrared rays may be performed by using any method known in the art. In a specific embodiment, a mixer may be used, and a simple stirring method may be also used.

The dissolving of the mixture by heating may be performed at 50° C. to 100° C., and the mixture may be dissolved by heating at a temperature of about 50° C. to about 100° C., about 50° C. to about 90° C., about 50° C. to about 85° C., about 50° C. to about 80° C., about 50° C. to about 70° C., about 60° C. to about 100° C., about 60° C. to about 90° C., about 60° C. to about 85° C., about 60° C. to about 80° C., about 70° C. to about 100° C., about 70° C. to about 90° C., about 70° C. to about 85° C., about 70° C. to about 80° C., or about 70° C. to about 75° C. It is possible to adjust the dissolving temperature according to decision of a person skilled in the art.

In the stirring, it is obvious that stirring may be performed through a process that may be easily used by a person skilled in the art, such as use of a stirrer, a mixer, etc.

Through this preparation method, prepared is the cosmetic composition for blocking near-infrared rays capable of significantly blocking lights in the near-infrared region, the cosmetic composition including the organic-inorganic composite particles for blocking near-infrared rays, wherein the organic-inorganic composite particles include the polymer matrix; and the inorganic nanoparticles dispersed in the polymer matrix, and have a hollow spherical form having a predetermined thickness.

Advantageous Effects of Disclosure

When a cosmetic composition for blocking near-infrared rays according to the present disclosure is applied to skin, light in the near-infrared region may be significantly blocked. The cosmetic composition may be used as a multifunctional product in combination with a UV-blocking material to block a wide range of wavelengths adversely affecting the skin, thereby preventing skin aging.

BEST MODE

Figure 1:
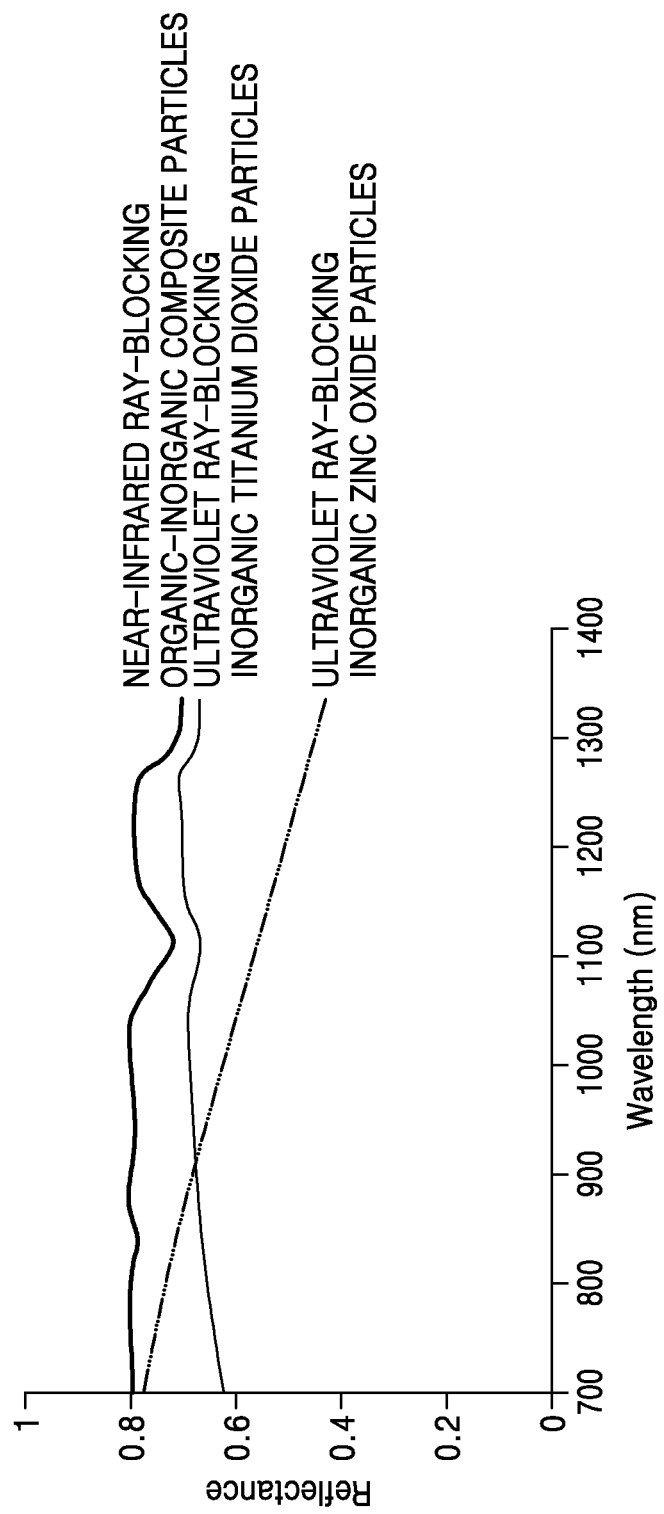
FIG. 1 is a graph showing spectral reflectance measurement of ultraviolet ray- and near-infrared ray-blocking inorganic particles.

Example 1. Preparation of Cosmetic Composition for Blocking Near-Infrared Rays Including 2.5% by Weight of Organic-Inorganic Composite Particles for Blocking Near-Infrared Rays A cosmetic composition of Example 1 was prepared as in a composition described in the following Table 1.

In detail, organic-inorganic composite particles having a hollow spherical form, in which titanium dioxide was dispersed in a polymer poly(methyl methacrylate) (PMMA), were first prepared as organic-inorganic composite particles for blocking near-infrared rays.

First, 0.60 g of methyl methacrylate (MMA) and 0.106 g of ethylene glycol dimethacrylate (EDGMA) were mixed, and then 0.015 g of 2 wt % CR-50 (manufactured by Ishihara Sangyo Kaisha) which is a commercial product of titanium dioxide nanoparticles was dispersed therein. Next, 0.15 g (20 wt % with respect to MMA, MW: 120,000) of poly (methyl methacrylate) (PMMA) which is a linear polymer material was added thereto, followed by sonication for about 1 hour and 30 minutes. Thereafter, 0.011 g of AIBN was dispersed in 0.14 g of MMA, and the above sonicated solution was added thereto. Next, the AIBN-added solution was added to a PVA aqueous solution (15 g, 2 wt %) which had been heated in an oil bath at 80° C., followed by stirring. Homogenization was performed at 15000 rpm for 30 minutes, and a purification process of centrifugation (4000 rpm, 15 min) was repeated three times to obtain organic-inorganic composite particles for blocking near-infrared rays.

2.5% by weight of the above organic-inorganic composite particles for blocking near-infrared rays including the inorganic material was mixed with and dispersed in oil phase described in Table 1, and dissolved by heating at 70° C. to 80° C. Thereafter, an aqueous phase was added thereto, followed by stirring.

In detail, organic-inorganic composite particles having a hollow spherical form, in which titanium dioxide was dispersed in a polymer poly(methyl methacrylate) (PMMA), were first prepared as organic-inorganic composite particles for blocking near-infrared rays.

First, 0.60 g of methyl methacrylate (MMA) and 0.106 g of ethylene glycol dimethacrylate (EDGMA) were mixed, and then 0.015 g of 2 wt % CR-50 (manufactured by Ishihara Sangyo Kaisha) which is a commercial product of titanium dioxide nanoparticles was dispersed therein. Next, 0.15 g (20 wt % with respect to MMA, MW: 120,000) of poly

TABLE 1

| | | Content(wt %) | | | | |
|---|---|---|---|---|---|---|
| | Component | Comparative Example 1 | Comparative Example 2 | Comparative Example 3 | Example 1 | Example 2 |
| Oil phase | Lauryl PEG-polydimethylsiloxyethyl dimethicone | 1.00 | 1.00 | 1.00 | 1.00 | 1.00 |
| | PEG-10dimethicone | 3.00 | 3.00 | 3.00 | 3.00 | 3.00 |
| | Ethylhexylmethoxycinnamate (organic UV-filter) | 5.00 | 5.00 | 5.00 | 5.00 | 5.00 |
| | Butylene glycol dicaprylate/dicaprate | 3.00 | 3.00 | 3.00 | 3.00 | 3.00 |
| | Diphenylsiloxy phenyl trimethicone | 2.00 | 2.00 | 2.00 | 2.00 | 2.00 |
| | Cyclopentasiloxane | 5.00 | 5.00 | 5.00 | 5.00 | 5.00 |
| | Cyclohexasiloxane Dimethicone | 5.00 | 5.00 | 5.00 | 5.00 | 5.00 |
| | Disteardimonium hectorite | 0.50 | 0.50 | 0.50 | 0.50 | 0.50 |
| Inorganic material | Titanium dioxide (inorganic UV-filter) | — | 5.00 | — | — | — |
| | Zinc oxide (inorganic UV-filter) | — | — | 5.00 | — | — |
| | Organic-inorganic composite particles for blocking near-infrared rays | — | — | — | 2.50 | 5.00 |
| Aqueous phase | Purified water | To 100 | To 100 | To 100 | To 100 | To 100 |
| | Disodium EDTA | 0.02 | 0.02 | 0.02 | 0.02 | 0.02 |
| | Polyol | 5.00 | 5.00 | 5.00 | 5.00 | 5.00 |
| | Preservative | Proper amount | Proper amount | Proper amount | Proper amount | Proper amount |
| Total | | 100 | 100 | 100 | 100 | 100 |

Example 2. Preparation of Cosmetic Composition for Blocking Near-Infrared Rays Including 5.0% by Weight of Organic-Inorganic Composite Particles for Blocking Near-Infrared Rays A cosmetic composition of Example 2 was prepared as in a composition described in the following Table 1. In detail, 5.0% by weight of the organic-inorganic composite particles for blocking near-infrared rays including the inorganic material which were prepared in the same manner as in Example 1 were mixed with and dispersed in oil phase, and dissolved by heating at 70° C. to 80° C. Thereafter, an aqueous phase was added thereto, followed by stirring.

Mode of Disclosure

Hereinafter, the present disclosure will be described in more detail with reference to Examples. However, these Examples are for illustrative purposes only, and the scope of the present disclosure is not intended to be limited by these Examples.

Example 1. Preparation of Cosmetic Composition for Blocking Near-Infrared Rays Including 2.5% by Weight of Organic-Inorganic Composite Particles for Blocking Near-Infrared Rays A cosmetic composition of Example 1 was prepared as in a composition described in Table 1.

(methyl methacrylate) (PMMA) which is a linear polymer material was added thereto, followed by sonication for about 1 hour and 30 minutes. Thereafter, 0.011 g of AIBN was dispersed in 0.14 g of MMA, and the above sonicated solution was added thereto. Next, the AIBN-added solution was added to a PVA aqueous solution (15 g, 2 wt %) which had been heated in an oil bath at 80° C., followed by stirring. Homogenization was performed at 15000 rpm for 30 minutes, and a purification process of centrifugation (4000 rpm, 15 min) was repeated three times to obtain organic-inorganic composite particles for blocking near-infrared rays.

2.5% by weight of the above organic-inorganic composite particles for blocking near-infrared rays including the inorganic material was mixed with and dispersed in oil phase described in Table 1, and dissolved by heating at 70° C. to 80° C. Thereafter, an aqueous phase was added thereto, followed by stirring.

Example 2. Preparation of Cosmetic Composition for Blocking Near-Infrared Rays Including 5.0% by Weight of Organic-Inorganic Composite Particles for Blocking Near-Infrared Rays A cosmetic composition of Example 2 was prepared as in a composition described in the following Table 1. In detail, 5.0% by weight of the organic-inorganic composite particles for blocking near-infrared rays including the inorganic material which were prepared in the same manner as in Example 1 were mixed with and dispersed in oil phase, and dissolved by heating at 70° C. to 80° C. Thereafter, an aqueous phase was added thereto, followed by stirring.

Examples 1 and 2 were prepared in order to compare the near-infrared ray-blocking effects according to contents of the known UV-blocking inorganic material and the near-infrared ray-blocking organic-inorganic composite particles.

Comparative Example 1. Preparation of Comparative Cosmetic Composition Including No Inorganic Material A cosmetic composition of Comparative Example 1 was prepared as in a composition described in Table 1. In detail, no materials were mixed with and dispersed in oil phase described in Table 1, and dissolved by heating at 70° C. to 80° C. Thereafter, an aqueous phase was added thereto, followed by stirring.

Comparative Example 2. Preparation of Comparative Cosmetic Composition Including Titanium Dioxide A cosmetic composition of Comparative Example 2 was prepared as in a composition described in Table 1. In detail, 5.0% by weight of titanium dioxide which is an inorganic material was mixed with and dispersed in oil phase described in Table 1, and dissolved by heating at 70° C. to 80° C. Thereafter, an aqueous phase was added thereto, followed by stirring.

Comparative Example 3. Preparation of Comparative Cosmetic Composition Including Zinc Oxide A cosmetic composition of Comparative Example 3 was prepared as in a composition described in Table 1. In detail, 5.0% by weight of zinc oxide which is an inorganic material was mixed with and dispersed in oil phase described in Table 1, and dissolved by heating at 70° C. to 80° C. Thereafter, an aqueous phase was added thereto, followed by stirring.

Comparative Example 1 was prepared in order to examine the near-infrared ray-blocking effect of the known UV-blocking organic material, and Comparative Examples 2 and 3 were prepared by using the known UV-blocking inorganic materials, titanium dioxide and zinc oxide, which may affect spectral reflectance in the near-infrared region, respectively. All of Comparative Examples and Examples were found to form opaque white emulsion-type compositions.

Experimental Example 1. Evaluation of Near-Infrared Ray-Blocking Ability Using Near-Infrared Spectrophotometer In order to evaluate near-infrared ray-blocking ability of the organic-inorganic composite particles for blocking near-infrared rays prior to application of the particles to formulations, a near infrared spectrophotometer (NIR spectrophotometer, ASD Inc., USA) was used to measure spectral reflectance.

The wavelength region of near-infrared rays is 760 nm to 1400 nm, and in this region, higher spectral reflectance indicates higher near-infrared ray-blocking ability. Results of measuring spectral reflectance of the known UV-blocking inorganic particles and the near-infrared ray-blocking organic-inorganic composite particles are shown in FIG. 1.

Evaluation of the near-infrared ray-blocking ability is obtained by the reflectance measurement. Since organic materials generally absorb lights, the near-infrared ray-blocking ability was evaluated only for the UV-blocking inorganic particles and the near-infrared ray-blocking organic-inorganic composite particles.

Referring to FIG. 1, as titanium dioxide and zinc oxide which are used as the known UV-blocking inorganic materials were compared with each other, titanium dioxide was found to show higher spectral reflectance. However, as compared with the near-infrared ray-blocking organic-inorganic composite particles, spectral reflectance of the near-infrared ray-blocking organic-inorganic composite particles was found to be higher than those of the known UV-blocking inorganic particles.

Experimental Example 2. In-Vivo Evaluation of Near-Infrared Ray-Blocking Effect of Cosmetic Composition For Blocking Near-Infrared Rays In order to evaluate near-infrared ray-blocking effects of the emulsions prepared in Comparative Examples and Examples, the following evaluation method developed by our company was employed. The near-infrared ray-blocking effects were evaluated by measuring spectral reflectance in the wavelength region of near-infrared rays, and an apparatus used for the measurement is the same as in Experimental Example 1.

[Method of Evaluating Near-Infrared Ray-Blocking Effect]

1) Preparing the skin of the inner side of the human arm in a size of 3.5 cm×4 cm
2) Measuring spectral reflectance before sample application (control)
3) Evenly applying 2 μL/cm² of the sample using fingers
4) Leaving for 15 minutes
5) Measuring spectral reflectance at the site to which the sample was applied (sample)
6) Measuring infrared ray-blocking effects by putting the spectral reflectance before and after sample application into the following equation (IPF: Infrared Protection Factor)

$$IPF = \frac{\int_{760\,nm}^{1400\,nm} Reflectance(sample) - \int_{760\,nm}^{1400\,nm} Reflectance(control)}{\int_{760\,nm}^{1400\,nm} Reflectance(control)} \quad \text{[Mathematical Equation 1]}$$

Figure 2:
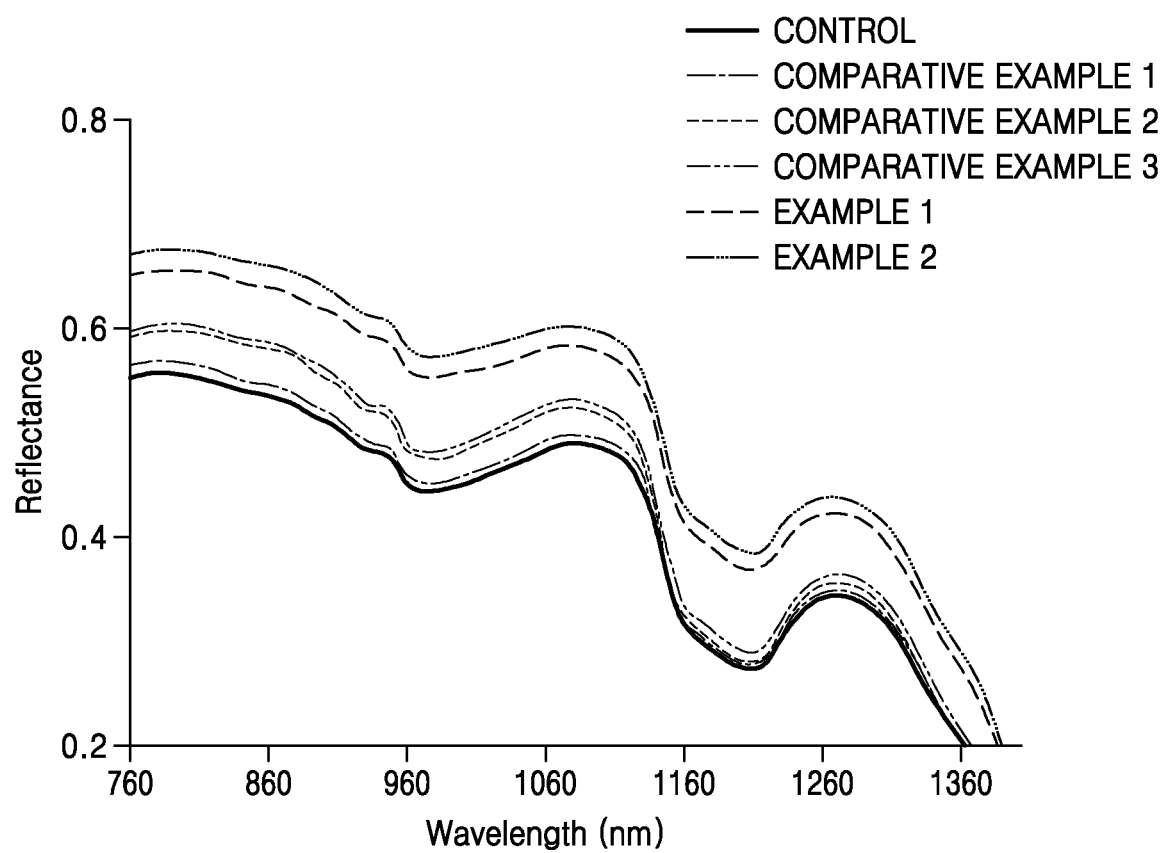
FIG. 2 is a graph showing a comparison, in terms of spectral reflectance in the near-infrared region, between a cosmetic composition including organic-inorganic composite particles for blocking near-infrared rays and a cosmetic composition not including the organic-inorganic composite particles for blocking near-infrared rays.

In order to examine the near-infrared ray-blocking effects, the near-infrared ray-blocking effects of Comparative Examples 1 to 3 and Examples 1 and 2 were compared with each other and the results are shown in FIG. 2. FIG. 2 is a graph showing measurement of the near-infrared ray-blocking effects by using the near-infrared spectrophotometer. Since higher reflectance in the near-infrared region indicates higher near-infrared ray-blocking effect, spectral reflectance after sample application was compared with spectral reflectance before sample application.

In FIG. 2, Control indicates the result of measuring spectral reflectance of the skin to which the sample was not applied, and others indicate the results of measuring spectral reflectance of the five cosmetic compositions prepared according to the compositions of Table 1. Since Comparative Example 1 included only the organic blocking agent as mentioned in Experimental Example 1, it absorbed infrared rays, and as a result, the spectral reflectance difference before and after application of the cosmetic composition was very small. Comparative Example 2 and Comparative Example 3 are cosmetic compositions including titanium dioxide and zinc oxide which are UV-blocking inorganic materials, respectively, and they showed high spectral reflectance, as compared with Comparative Example 1.

However, as shown in FIG. 2, when the compositions prepared by using the known UV-blocking inorganic materials (Comparative Example 2 and Comparative Example 3) were compared with the compositions prepared by using the near-infrared ray-blocking organic-inorganic composite particles (Example 1 and Example 2), the compositions prepared by using the near-infrared ray-blocking organic-inorganic composite particles showed much higher spectral reflectance in the near-infrared region than before application of the cosmetics, indicating that the near-infrared ray-blocking organic-inorganic composite particles reflect more near-infrared rays than the UV-blocking inorganic materials, and thus their effect of blocking near-infrared rays from the skin is high.

Experimental Example 3. Test of Sense of Use of Cosmetic Composition

Sense of use of the compositions prepared by Example 2 and Comparative Examples 2 and 3, each having the same content of the inorganic material, were evaluated for twenty adult men and women without skin diseases, as follows. Example 2 and Comparative Examples 2 and 3 were applied to their cheek, and sense of use, such as cloudiness, texture (smoothness), and overall satisfaction which may occur at the time of using inorganic materials, was evaluated and the results are shown in the following Table 2. If more than 15 persons satisfied, it was marked as ●. If more than 10 persons satisfied, it was marked as ○. If more than 5 persons satisfied, it was marked as Δ.

TABLE 2

|  | Comparative Example 2 | Comparative Example 3 | Example 1 |
| --- | --- | --- | --- |
| Cloudiness | ○ | ○ | ● |
| Texture | Δ | ○ | ● |
| Overall satisfaction | ○ | ○ | ● |

In general, inorganic material-containing compositions commonly show unsmooth texture or heavy cloudiness when applied to the skin, and therefore, they are required to be improved. As shown in Table 2, the cosmetic composition containing the near-infrared ray-blocking organic-inorganic composite particles according to the present disclosure showed improvement in cloudiness or rough texture, as compared with use of the known UV-blocking inorganic particles, and therefore, its overall satisfaction with sense of use was found to be excellent.

The invention claimed is:

1. A cosmetic composition for blocking near-infrared rays, the cosmetic composition comprising organic-inorganic composite particles for blocking near-infrared rays, wherein the organic-inorganic composite particles comprise a polymer matrix, and inorganic nanoparticles dispersed in the polymer matrix, and have a hollow spherical form having a predetermined thickness,
   wherein the polymer matrix is poly(methyl methacrylate), and the inorganic nanoparticles are $TiO_2$,
   wherein a content of the inorganic nanoparticles is 1% by weight to 5% by weight, based on the total weight of the organic-inorganic composite particles,
   wherein a root mean square (RMS) surface roughness of an outer circumferential surface of each of the organic-inorganic composite particles is 10 nm to 50 nm.

2. The cosmetic composition for blocking near-infrared rays of claim 1, wherein a ratio of a radius to the thickness of each of the organic-inorganic composite particles is 2:1 to 4:1, wherein the radius is measured from the center to the outermost point of each of the organic-inorganic composite particles.

3. The cosmetic composition for blocking near-infrared rays of claim 1, wherein a root mean square (RMS) surface roughness of an inner circumferential surface of each of the organic-inorganic composite particles is 5 nm to 30 nm.

4. The cosmetic composition for blocking near-infrared rays of claim 1, wherein the inorganic nanoparticles further comprise at least one additional inorganic nanoparticle selected from the group consisting of ZnO, $ZnO_2$, CuO, $CuO_2$, $Al_2O_3$, $A(OH)_3$, $Ce_2$, $Ce_2O_3$, $Fe_2O_3$, $ZrO_2$, and any mixture thereof.

5. The cosmetic composition for blocking near-infrared rays of claim 1, wherein the polymer matrix comprises at least one additional polymer in the matrix selected from the group consisting of polystyrene, polymethylacrylate, polyethylacrylate, polypropylacrylate, polyisopropylacrylate, polyethylmethacrylate, polybutylacrylate, polybutylmethacrylate, polypentylacrylate, polypentylmethacrylate, polyglycidylmethacrylate, polycyclohexylacrylate, poly(2-ethylhexylacrylate), polyacrylic acid, polymethacrylic acid, and any mixture thereof.

6. The cosmetic composition for blocking near-infrared rays of claim 1, wherein plasmonic nanoparticles or a plasmonic nanofilm is attached to the surface of each of the inorganic nanoparticles.

7. The cosmetic composition for blocking near-infrared rays of claim 6, wherein the plasmonic nanoparticles and the plasmonic nanofilm are selected from gold, silver, platinum, palladium, copper, aluminum, and any mixture thereof.

8. The cosmetic composition for blocking near-infrared rays of claim 1, wherein the cosmetic composition is a water-in-oil type cosmetic composition.

9. The cosmetic composition for blocking near-infrared rays of claim 1, wherein the cosmetic composition further comprises a cosmetic composition for blocking ultraviolet rays.

\* \* \* \* \*